United States Patent
Davis et al.

(10) Patent No.: US 7,297,754 B2
(45) Date of Patent: Nov. 20, 2007

(54) METHOD FOR THE PREPARATION OF AROMATIC CHLOROFORMATES

(75) Inventors: Gary Charles Davis, Albany, NY (US); James Manio Silva, Clifton Park, NY (US); Joshua James Stone, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 24 days.

(21) Appl. No.: 11/170,306

(22) Filed: Jun. 28, 2005

(65) Prior Publication Data

US 2006/0293535 A1    Dec. 28, 2006

(51) Int. Cl.
*C08G 64/00*    (2006.01)

(52) U.S. Cl. .............. 528/196; 422/131; 528/198; 558/260; 558/270; 558/274; 558/281

(58) Field of Classification Search ............. 422/131; 528/196, 198; 558/260, 270, 274, 281
See application file for complete search history.

(56) References Cited

U.S. PATENT DOCUMENTS

| 4,085,129 A | 4/1978 | Semler et al. |
| 4,366,102 A | 12/1982 | Rauchschwalbe et al. |
| 5,274,164 A | 12/1993 | Wettling et al. |
| 5,424,473 A | 6/1995 | Galvan et al. |
| 5,616,771 A | 4/1997 | Kahl et al. |
| 6,392,079 B1 | 5/2002 | Silva et al. |

FOREIGN PATENT DOCUMENTS

| CS | 190921 | 6/1979 |
| DE | 118537 | 2/1901 |
| JP | 48043489 | 12/1973 |
| JP | 48043490 | 12/1973 |
| JP | 51041328 | 4/1976 |

OTHER PUBLICATIONS

Witold Missner & Ryszard Zielinski, "Method of prepartation of Alkyl Chloroforamtes", 1978, Zeszyty Naukowe—Akademia Ekonomiczna w Poznaniu, Seria 1: Prace z Zakresu Towaroznawstwa i Chemii, vol. 73, pp. 92-96, CODEN: ZNASDH; ISSN: 0208-4902.
International Search Report dated Oct. 30, 2006.
XP-002401946, M. Nagel et al., "Synthesis of Polyalkylphenyl Prop-2-ynoates and Their Flash Vacuum Pyrolysis to Polyalkylcyclohepta[b]furan-2(2H)-ones", Helvetica Chimica Acta., vol. 83, pp. 1022-1048, 2000.
XP-002401948, H. Hagemann et al., "Houben-Weyl. Methoden der Organischen Chemie—Kohlensäure-Derivate", Thieme Verlag, Stuttgart, Deutschland, pp. 15-24, 1983.

*Primary Examiner*—Terressa Boykin

(57) ABSTRACT

A method for preparing an aromatic chloroformate comprising, introducing a mixture of at least one aromatic hydroxyl compound, phosgene, at least one solvent, and at least one organic base into a flow reactor to obtain a unidirectionally flowing reaction mixture. The unidirectionally flowing reaction mixture is maintained at a temperature between about 0° C. and about 60° C. to produce a single product stream comprising an aromatic chloroformate.

22 Claims, No Drawings

METHOD FOR THE PREPARATION OF AROMATIC CHLOROFORMATES

BACKGROUND OF THE INVENTION

This invention relates to a method for preparing an aromatic chloroformate useful in the preparation of polycarbonates and co-polycarbonates. More particularly the method relates to a method for preparing an aromatic chloroformate in a flow reactor.

Aromatic alcohols may be phosgenated in both batch processes and continuous processes to provide aromatic chloroformates. Despite extensive research and development efforts directed towards the more efficient manufacture of aromatic chloroformates, deficiencies remain.

It is of interest therefore, to develop new and more efficient processes for the formation of aromatic chloroformates.

BRIEF SUMMARY OF THE INVENTION

The present invention provides a method for the preparation of aromatic chloroformates. The method comprises introducing into a flow reactor at least one aromatic hydroxyl compound, phosgene, at least one solvent, and an organic base to form a unidirectionally flowing reaction mixture, said unidirectionally flowing reaction mixture being substantially free of water; and maintaining said unidirectionally flowing reaction mixture at a temperature in a range between about 0° C. and about 60° C. to produce a product stream comprising an aromatic chloroformate.

In another aspect the present invention provides a method for preparing a co-polycarbonate. The method comprises reacting a dihydroxy aromatic compound under interfacial conditions with phosgene and an aromatic chloroformate. The aromatic chloroformate is prepared by a method comprising introducing into a flow reactor at least one aromatic hydroxyl compound, phosgene, at least one solvent, and an organic base to form a unidirectionally flowing reaction mixture, said unidirectionally flowing reaction mixture being substantially free of water; and maintaining said unidirectionally flowing reaction mixture at a temperature in a range between about 0° C. and about 60° C. to produce a product stream comprising an aromatic chloroformate.

DETAILED DESCRIPTION OF THE INVENTION

The present invention may be understood more readily by reference to the following detailed description of preferred embodiments of the invention and the examples included therein. In the following specification and the claims which follow, reference will be made to a number of terms which shall be defined to have the following meanings:

The singular forms "a", "an" and "the" include plural referents unless the context clearly dictates otherwise.

The modifier "about" used in connection with a quantity is inclusive of the stated value and has the meaning dictated by the context (e.g., includes the degree of error associated with measurement of the particular quantity).

The term "aromatic hydroxyl compound" as used herein refers to an organic species comprising at least one hydroxyl group attached to an aromatic carbon atom, wherein the aromatic hydroxyl compound is free from aliphatic hydroxyl groups. Phenol, hydroquinone, beta-naphthol; 1,3,5-trihydroxybenzene; and 3-hydroxypyridine illustrate aromatic hydroxyl compounds. Conversely, organic species which do not comprise a hydroxyl group attached to an aromatic carbon atom are not ranked among aromatic hydroxyl compounds. A hydroxyl group attached to a non-aromatic carbon atom is referred to herein as an "aliphatic hydroxyl group". Methanol, ethanol, ethylene glycol, cyclohexanol, sucrose, dextrose, benzyl alcohol, and cholesterol illustrate compounds comprising aliphatic hydroxyl groups. However, compounds comprising hydroxyl groups attached to the aromatic group and also containing non-aromatic carbons, for example 2,6-dimethylphenol, fall within the group defined by the term aromatic hydroxyl compounds.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC($CF_3$)$_2$PhO—), 4-chloromethylphen-1-yl, 3-trifluorovinyl-2-thienyl, 3-trichloromethylphen-1-yl (i.e., 3C$Cl_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}C(CF_3)_2C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., $CH_3CHBrCH_2C_6H_{10}$—), and the like. Further examples of cycloaliphatic radicals include 4-allyloxycyclohex-1-yl, 4-aminocyclohex-1-yl (i.e., $H_2NC_6H_{10}$—), 4-aminocarbonylcyclopent-1-yl (i.e., $NH_2COC_5H_8$—), 4-acetyloxycyclohex-1-yl, 2,2-dicyanoisopropylidenebis(cyclohex-4-yloxy) (i.e., —$OC_6H_{10}C(CN)_2C_6H_{10}O$—), 3-methylcyclohex-1-yl, methylenebis(cyclohex-4-yloxy) (i.e., —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}$—), 4-mercaptomethylcyclohex-1-yl (i.e., 4-$HSCH_2C_6H_{10}$—), 4-methylthiocyclohex-1-yl (i.e., 4-$CH_3SC_6H_{10}$—), 4-methoxycyclohex-1-yl, 2-methoxycarbonylcyclohex-1-yloxy(2-$CH_3OCOC_6H_{10}O$—), 4-nitromethylcyclohex-1-yl (i.e., $NO_2CH_2C_6H_{10}$—), 3-trimethylsilylcyclohex-1-yl, 2-t-butyldimethylsilycyclopent-1-yl, 4-trimethoxysilylethylcyclohex-1-yl (e.g., $(CH_3O)_3SiCH_2CH_2C_6H_{10}$—), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —$CH_2CHBrCH_2$—), and the like. Further examples of aliphatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e., —CHO), hexyl, hexamethylene, hydroxymethyl (i.e., —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., $(CH_3)_3Si$—), t-butyldimethylsilyl, 3-trimethyoxysilylpropyl (i.e., $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical.

As used herein the term "tertiary aliphatic radical" refers to a radical attached to an aromatic ring via a bond, the bond linking the tertiary aliphatic radical and the aromatic ring being between a carbon atom of the aromatic ring and a tertiary carbon atom of the tertiary aliphatic radical. For example, the compound t-butylbenzene is a compound comprising a tertiary aliphatic radical, the t-butyl radical, said t-butyl radical being attached to an aromatic phenyl ring via a bond, the bond linking the t-butyl radical and the aromatic ring being between a carbon atom of the aromatic ring and the tertiary carbon atom of the t-butyl radical.

As used herein the term "tertiary cycloaliphatic radical" refers to a radical attached to an aromatic ring via a bond, the bond linking the tertiary cycloaliphatic radical and the aromatic ring being between a carbon atom of the aromatic ring and a tertiary carbon atom of the tertiary cycloaliphatic radical. For example, the compound 1-methylcyclohex-1yl-benzene is a compound comprising a tertiary cycloaliphatic radical, the 1-methylcyclohex-1yl radical, said 1-methylcyclohex-1yl radical being attached to an aromatic phenyl ring via a bond, the bond linking the tertiary cycloaliphatic radical and the aromatic ring being between a carbon atom of the aromatic ring and the tertiary carbon atom of the tertiary cycloaliphatic radical. As a further example 1-cyclohexyl-1-methyleth-1-yl benzene is likewise an example of a tertiary cycloaliphatic radical.

As used herein, the term "aromatic hydroxyl compound comprising only hydroxyl groups flanked on each side by tertiary aliphatic and/or tertiary cycloaliphatic radicals" refers to aromatic hydroxyl compounds in which the only hydroxyl groups present are "flanked by" 2 tertiary aliphatic radicals, or 2 tertiary cycloaliphatic radicals, or 1 tertiary aliphatic radical and 1 tertiary cycloaliphatic radical. For example, 2,6-di-t-butylphenol comprises a single hydroxyl group on an aromatic ring, and both positions on the aromatic ring adjacent to the hydroxyl group are substituted by a tertiary aliphatic radical, the t-butyl radical. Under such conditions, the hydroxyl group of 2,6-di-t-butylphenol is said to be flanked on each side by a tertiary aliphatic radical, the t-butyl radical. The compound, 2,6-di-t-butyl-4-hydroxyphenol, 3,5-di-t-butylphenol and 2-t-butyl-6-isopropylphenol are examples of aromatic hydroxyl compounds which do not fall with the scope of an "aromatic hydroxyl compound comprising only hydroxyl groups flanked on each side by tertiary aliphatic and/or tertiary cycloaliphatic radicals".

As used herein the term "solvent" refers to a single solvent such as methylene chloride, or in the alternative to mixtures of solvents such as a mixture of methylene chloride and toluene.

As used herein, the term "interfacial conditions" refers to conditions typically employed in the preparation of polycarbonate from at least one bisphenol and phosgene in the presence of a stoichiomteric amount of a metal hydroxide in a mixed solvent system comprising water and at least one solvent which is not miscible with water.

"BPA" is herein defined as bisphenol A and is also known as 2,2-bis(4-hydroxyphenyl)propane; 4,4'-isopropylidenediphenol, and p,p-BPA.

As noted, the present invention generally relates to a method of preparing an aromatic chloroformate. The method includes introducing at least one aromatic hydroxyl compound, phosgene and a solvent into a flow reactor to form a unidirectionally flowing reaction mixture wherein the aromatic hydroxy compound is free of aliphatic hydroxyl groups. An organic base is also introduced into the flow reactor. In one embodiment of the present invention, the unidirectionally flowing reaction mixture is substantially free of water. The term "substantially free of water" is defined as containing less than 2% percent by weight of water based on the weight of the reaction mixture comprising aromatic hydroxyl compound, phosgene and a solvent. When the reaction mixture is not substantially free of water, it is believed that the water may compete with the hydroxyl groups of the aromatic hydroxyl compound for phosgene. When the hydroxyl groups of the aromatic hydroxyl compound react with phosgene product chloroformates result, together with by-product hydrochloric acid. However, when water reacts with phosgene the products are carbon dioxide and hydrochloric acid. The presence of water in the unidirectionally flowing reaction mixture may be thus undesirable because phosgene is consumed without the production of the desired chloroformate product.

Aromatic chloroformates which may be prepared according to the present invention include monochloroformates and polychloroformates. Polychloroformates comprise at least two chloroformate groups, for example, bischloroformates, and trischloroformates. In one particular embodiment the aromatic chloroformate formed is a monochloroformate.

Aromatic hydroxyl compounds suitable for use according to the present invention include aromatic hydroxyl compounds free of aliphatic hydroxyl groups. In one embodiment, the aromatic hydroxyl compound comprises formula I,

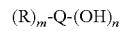   Formula I wherein Q is a $C_3$-$C_{20}$ aromatic radical, R is independently at each occurrence a hydrogen atom, a $C_1$-$C_5$ aliphatic radical, a $C_3$-$C_7$ cycloaliphatic radical or a $C_3$-$C_6$ aromatic radical, "n" is a number equal to the total number of aromatic positions on Q available for substitution and "m" is an integer having value 0 to {(the total number of positions on Q available for substitution)−n}. As a further example, when formula I represents phenol substituted with "m" R groups, the total number of aromatic positions on Q available for substitutions is equal to 6, n is equal to 1, and the maximum value of m is equal to 6−1=5. In this example the total number of positions on Q available for substitution, 6, is the same as the total number of aromatic positions on Q available for substitution.

Suitable aromatic hydroxyl compounds include aromatic mono-alcohols and aromatic polyols. Exemplary aromatic hydroxyl compounds include, but are not limited to, phenol, substituted phenols, naphthols and substituted naphthols. Substituted phenols are exemplified by p-cumylphenol, meta-cresol, 4-tert-butylphenol, 2-tert-butylphenol, mesitol, 2,6-dimethylphenol, 2,4-dimethylphenol, 2,4-dimethyl-6-tert-butylphenol, 2,6-diphenylphenol, 2-phenylphenol, 2,4-diphenylphenol, BPA, 4,4'-biphenol, and the like. Substituted naphthols are exemplified by 2,4-diphenylnaphthol, 2,4-dimethylnaphthol, 4-chloronaphthol, 1,1-binaphthol, and the like.

The method of the present invention employs phosgene as the chloroformylating agent. Thus, phosgene reacts with the aromatic hydroxyl groups of the aromatic hydroxyl compounds employed, to provide aromatic chloroformates. The molar ratio of phosgene to the hydroxyl groups in the aromatic hydroxy compound is typically in a range of from about 1.1 to 1 to about 100 to 1. In one embodiment, the molar ratio of phosgene to the hydroxyl groups, is in a range of from about 1.1 to 1 to about 50 to 1. In another embodiment, the molar ratio of phosgene to the aromatic hydroxyl groups is in a range of from about 1.1 to 1 to about 5 to 1.

The chloroformylation reaction is carried out in the presence of a solvent, which helps to maintain the flow of the reaction mixture in the flow reactor and dissipate heat, among other advantages. The solvent is selected from the group consisting of aliphatic solvents and aromatic solvents. In one embodiment the solvent is selected from the group consisting of $C_6$-$C_{10}$ hydrocarbon solvents and $C_1$-$C_{10}$ chlorinated solvents. Exemplary $C_6$-$C_{10}$ hydrocarbon solvents include benzene, toluene, hexane, heptane, octane, isooctane, decane, xylene, mesitylene, and the like. In one embodiment, the solvent is selected from the group consisting of $C_1$-$C_{10}$ chlorinated solvents. Suitable $C_1$-$C_{10}$ chlorinated solvents include methylene chloride, ethylene chloride, chloroform, chorobenzene, chlorotoluene, chloronaphthalene, and the like. Chorinated aliphatic solvents such as methylene chloride are typically preferred.

At least one organic base is introduced as a component reactant in the unidirectionally flowing reaction mixture. The role of the organic base is to mediate the formation of chloroformate groups in the reaction of the aromatic hydroxy groups with phosgene. The organic base is believed to enhance the rate of reaction between the aromatic hydroxy groups and phosgene, and to serve as a trap for the HCl by-product in the reaction. The organic base is selected from the group consisting of amine bases and polyamine bases. In one embodiment, the unidirectionally flowing reaction mixture is characterized by a molar ratio of the organic base to the aromatic hydroxyl groups in a range of from about 0.01 to 1 to about 100 to 1. In another embodiment, the unidirectionally flowing reaction mixture is characterized by a molar ratio of the organic base to the aromatic hydroxyl groups in a range of from about 0.01 to 1 to about 50 to 1. In still another embodiment, the unidirectionally flowing reaction mixture is characterized by a molar ratio of the organic base to the aromatic hydroxyl groups in a range of from about 0.01 to 1 to about 5 to 1.

As noted, the method of the present invention comprises introducing into a flow reactor at least one aromatic hydroxyl compound, phosgene, a solvent, and at least one organic base to form a unidirectionally flowing reaction mixture in which a product aromatic chloroformate is formed. For convenience, the aromatic hydroxyl compound, phosgene, and the organic base are collectively referred to as "the reactants". The reactants and solvent are typically introduced continuously into the flow reactor to produce a flowing reaction mixture. Continuous introduction of the reactants and solvent is not required, however. In one embodiment, the introduction of one or more of the aromatic hydroxyl compounds, phosgene, a solvent, and an organic base is carried out in a non-continuous manner. For example, the phosgene may be introduced in a series of discrete pulses with a time interval between each individual introduction of phosgene. The time intervals may be regular time intervals (i.e. be time intervals of equal duration), irregular time intervals, or a combination thereof.

The rates of addition of one or more of the reactants and solvent may be controlled by feedback provided by one or more sensors located within the flow reactor or in the product stream after it emerges from the flow reactor. For example, an excursion in the reactor effluent chloroformate concentration may trigger a change in the rate of addition of one or more of the reactants, for example the organic base.

The flow reactor used for carrying out the chloroformylation reaction is typically a tube having a front end into which the reactants and solvent are introduced, and a back end from which a product stream emerges from the reactor, but is not limited to tube reactors or tubular reactors. Many types of flow reactors are known and can be used in the practice of the present invention. For the purpose of describing the instant invention, a flow reactor is defined as a reactor which can be operated such that at least one reactant is added to the reactor while simultaneously removing at least one product from the reactor. For example the flow reactor may be a multi-channel flow reactor having a plurality of channels through which the flowing reaction mixture passes. In one embodiment, the flow reactor is continuous stirred tank reactor (CSTR). In another embodiment, the flow reactor is a tubular reactor configured with a continuous stirred tank reactor such that the output from the CTSR serves as the input for the tubular reactor. In one embodiment, the flow reactor comprises a single channel having a rectangular-shaped cross section.

Within the flow reactor, a unidirectionally flowing reaction mixture is produced. Although mixing elements may be present within the flow reactor, the unidirectionally flowing reaction mixture flows essentially in one direction, i.e. from the front end of the reactor to the back end of the reactor. This condition is sometimes also referred to as "co-current flow". A unidirectionally flowing reaction mixture characterized by co-current flow is typically formed by introducing reactants and solvent into an upstream portion of a flow reactor and removing at a position downstream a product stream containing all of the unreacted reactants, solvent, products, and by-products. The flow reactor may be equipped with a single inlet at the front end of the reactor for the introduction of reactants and solvent. Alternatively, the reactor may comprise a plurality of inlets for the introduction of reactants and solvents. As the unidirectionally flowing reaction mixture passes through the flow reactor, the reactants are converted to products and by-products. Typically, the product is the aromatic chloroformate and the by-product hydrochloric acid. The by-product hydrochloric acid is converted to the hydrochloride salt in presence of the organic base. The unidirectionally flowing reaction mixture in which a substantial portion of the reactants have been converted to product and by-product is referred to as the product stream. The flow reactor has at least one reactor outlet through which the product stream emerges from the reactor. Alternatively, the flow reactor may comprise a plurality of reactor outlets. The product stream exits from the reactor outlet or outlets. Typically, no vent or waste streams different from the product stream exit any separate reactor outlet—only the product stream exits, albeit possibly at multiple reactor outlets. The term, "single product stream" means that the entire product stream comprising all of the unreacted reactants (i.e. unreacted starting materials), products, by-products and solvent emerges from the reactor through a single reactor outlet. As a consequence, the entire mass of the reactants and solvent is conserved within the single product stream emerging from the flow reactor.

Alternatively, the flow reactor used may comprise a plurality of reactor outlets through which the product stream emerges. For example, in one embodiment the flow reactor is a tubular reactor of length "L" measured from the front end of the reactor to the back end of the reactor, said tubular reactor having two reactor outlets, a first reactor outlet located a distance "L/2" from the front end of the reactor, and a second reactor outlet located a distance "L" from the front end of the reactor. Reactants and solvent are introduced through three separate inlets at the front end of the reactor. The rates of addition of reactants and solvent and the reactor temperature may be controlled such that the product stream emerging at the first reactor outlet is characterized by a percent conversion of reactants to products of about 50 percent, and that the product stream emerging from the second reactor outlet is characterized by a percent conversion of reactants to products of about 100 percent. Each of the two product streams exiting the tubular flow reactor at positions "L/2" and "L" respectively contains all of the unreacted reactants, (i.e. unreacted starting materials), products, by-products and solvent present in the product stream at positions "L/2" and "L" within the flow reactor. It should be noted as well that the sum of the masses of the two product streams emerging at positions "L/2" and "L" is equal to the mass of reactants and solvents introduced into the tubular reactor. Thus, the entire mass of the reactants and solvent is conserved within the two streams emerging at various points along the flow reactor.

It should be further noted that the temperature in various sections of the reactor may be the same or different. For example, in the tubular reactor system just described the temperature of the flowing reaction mixture at first reactor outlet located a distance "L/2" from the front end of the reactor may be 25° C. while at the second reactor outlet located a distance "L" from the front end of the reactor the temperature of the flowing reaction mixture is 54° C. In addition, the flow reactor may be uniformly or nonuniformly heated or uniformly or nonuniformly cooled. Alternatively, the reaction may be carried out under adiabatic conditions.

Where multiple product streams are produced by a flow reactor according to the present invention it will be appreciated by those skilled in the art that each of the product streams may be used for a different purpose; as for example in the tubular reactor system just described the product stream emerging at the first reactor outlet located a distance "L/2" from the front end of the reactor may be directed to a polymerization reactor and used in the preparation of a co-polycarbonate, while at the product stream emerging at the second reactor outlet located a distance "L" from the front end of the reactor may be used to provide a purified chloroformate.

As noted, the flow reactor is not particularly limited and may be any reactor system, which provides for the "upstream" introduction of the reactants and the "downstream" removal of the product stream comprising the aromatic chloroformate, the solvent, the hydrochloride salt of the organic base, and any unreacted reactants. The flow reactor may comprise a series of flow reactor components, as for example, a series of continuous flow reactors arrayed such that the effluent from a first flow reactor provides the input for a second flow reactor and so forth. The reactants may be introduced into the flow reactor system through one or more feed inlets attached to the flow reactor system. Typically, it is preferred that the reactants and solvent be introduced into the flow reactor through at least three feed inlets. For example, as in the case where a solution of the aromatic hydroxyl compound in an organic solvent such as methylene chloride, organic base, and phosgene are introduced through separate feed inlets at or near the upstream end of a flow reactor. Alternatively, the feed solution may comprise a mixture of aromatic hydroxyl compound, solvent and the base, while phosgene is fed in separately. Alternative arrangements wherein one or more of the reactants is introduced through multiple feed inlets at various points along the flow reactor are also possible. Typically, the relative amounts of the reactants and solvent present in the flow reactor are controlled by the rate at which they are introduced. For example, a reactant can be introduced into the flow reactor through pumps calibrated to deliver a particular number of moles of said reactant per unit time.

In one embodiment the present invention provides a method for preparing a co-polycarbonate. The method comprises reacting a dihydroxy aromatic compound under interfacial conditions with phosgene and an aromatic chloroformate. The term "interfacial conditions" is meant to describe the conditions typically used to prepare polycarbonates commercially, namely conditions under which a mixture comprising the salt of a dihydroxy aromatic compound, base, water and a water immiscible solvent are reacted in a two phase reaction mixture with phosgene to afford polycarbonate. Thus in one embodiment, an aromatic chloroformate prepared by the method of the present invention is reacted under interfacial conditions with a dihydroxy aromatic compound and phosgene to afford a co-polycarbonate. Typically, the interfacial polymerization is carried out at a temperature between about 25° C. and about 40° C. at atmospheric pressure under relatively high pH conditions of 8-14, preferably pH 10-14. Generally an acid scavenger is employed which neutralizes the hydrogen chloride formed during the interfacial reaction. Typically the acid scavenger used is an aqueous base, for example, an alkali metal hydroxide. Non-limiting examples of alkali metal hydroxides include sodium hydroxide and potassium hydroxide. In a preferred embodiment the alkali metal hydroxide is sodium hydroxide. A catalyst is employed to promote the interfacial reaction and high yields are generally obtained. Typically, catalysts that may be employed herein are preferably amine catalysts. In one particular embodiment the catalyst is triethylamine (TEA). As noted, the aromatic chloroformate is prepared by the method of the present invention wherein at least one aromatic hydroxyl compound, phosgene, a solvent, and an organic base are introduced into a flow reactor to form a unidirectionally flowing reaction mixture. The unidirectionally flowing reaction mixture is in particular embodiments substantially free of water and is maintained at a temperature in a range between about 0° C. and about 60° C. to produce a product stream comprising an aromatic chloroformate and by-product HCl or the hydrochloride salt of the organic base. In a preferred embodiment unidirectionally flowing reaction mixture is substantially free of water and the temperature is maintained in a range between about 10° C. and about 50° C.

In one embodiment the dihydroxy aromatic compound is a bisphenol having formula II,

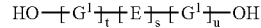

Formula II wherein each $G^1$ is independently at each occurrence a $C_6$-$C_{20}$ aromatic radical; E is independently at each occurrence a bond, a $C_3$-$C_{20}$ cycloaliphatic radical, a $C_3$-$C_{20}$ aromatic radical, a $C_1$-$C_{20}$ aliphatic radical, a sulfur-containing linkage, a selenium-containing linkage, a phosphorus-containing linkage, or an oxygen atom; "t" is a number greater than or equal to one; "s" is either zero or one; and "u" is a whole number including zero.

In certain embodiments the bisphenol is selected from the group consisting of 1,1-bis(4-hydroxyphenyl)cyclopentane; 2,2-bis(3-allyl-4-hydroxyphenyl)propane; 2,2-bis(2-t-butyl-4-hydroxy-5-methylphenyl)propane; 2,2-bis(3-t-butyl-4-hydroxy-6-methylphenyl)propane; 2,2-bis(3-t-butyl-4-hydroxy-6-methylphenyl)butane; 1,3-bis[4-hydroxyphenyl-1-(1-methylethylidine)]benzene; 1,4-bis[4-hydroxyphenyl-1-(1-methylethylidine)]benzene; 1,3-bis[3-t-butyl-4-hydroxy-6-methylphenyl-1-(1-methylethylidine)]benzene; 1,4-bis[3-t-butyl-4-hydroxy-6-methylphenyl-1-(1-methylethylidine)]benzene; 4,4'-biphenol; 2,2',6,8-tetramethyl-3,3',5,5'-tetrabromo-4,4'-biphenol; 2,2',6,6'-tetramethyl-3,3',5-tribromo-4,4'-biphenol; 1,1-bis(4-hydroxyphenyl)-2,2,2-trichloroethane; 1,1-bis(4-hydroxyphenyl)-1-cyanoethane; 1,1-bis(4-hydroxyphenyl)dicyanomethane; 1,1-bis(4-hydroxyphenyl)-1-cyano-1-phenylmethane; 2,2-bis(3-methyl-4-hydroxyphenyl)propane; 1,1-bis(4-hydroxyphenyl)norbornane; 3,3-bis(4-hydroxyphenyl)phthalide; 1,2-bis(4-hydroxyphenyl)ethane; 1,3-bis(4-hydroxyphenyl) propenone; bis(4-hydroxyphenyl)sulfide; 4,4'-oxydiphenol; 4,4-bis(4-hydroxyphenyl)pentanoic acid; 4,4-bis(3,5-dimethyl-4-hydroxyphenyl)pentanoic acid; 2,2-bis(4-hydroxyphenyl)acetic acid; 2,4'-dihydroxydiphenylmethane; 2-bis (2-hydroxyphenyl)methane; bis(4-hydroxyphenyl)methane; bis(4-hydroxy-5-nitrophenyl)methane; bis(4-hydroxy-2,6-dimethyl-3-methoxyphenyl)methane; 1,1-bis(4-hydroxyphenyl)ethane; 1,1-bis(4-hydroxy-2-chlorophenyl)ethane; 2,2-bis(4-hydroxyphenyl)propane (bisphenol-A); 1,1-bis(4-hydroxyphenyl)propane; 2,2-bis(3-chloro-4-hydroxyphenyl)propane; 2,2-bis(3-bromo-4-hydroxyphenyl)propane; 2,2-bis(4-hydroxy-3-methylphenyl)propane; 2,2-bis(4-hydroxy-3-isopropylphenyl)propane; 2,2-bis(3-t-butyl-4-hydroxyphenyl)propane; 2,2-bis(3-phenyl-4-hydroxyphenyl) propane; 2,2-bis(3,5-dichloro-4-hydroxyphenyl)propane; 2,2-bis(3,5-dibromo-4-hydroxyphenyl)propane; 2,2-bis(3,5-dimethyl-4-hydroxyphenyl)propane; 2,2-bis(3-chloro-4-hydroxy-5-methylphenyl)propane; 2,2-bis(3-bromo-4-hydroxy-5-methylphenyl)propane; 2,2-bis(3-chloro-4-hydroxy-5-isopropylphenyl)propane; 2,2-bis(3-bromo-4-hydroxy-5-isopropylphenyl)propane; 2,2-bis(3-t-butyl-5-chloro-4-hydroxyphenyl)propane; 2,2-bis(3-bromo-5-t-butyl-4-hydroxyphenyl)propane; 2,2-bis(3-chloro-5-phenyl-4-hydroxyphenyl)propane; 2,2-bis(3-bromo-5-phenyl-4-hydroxyphenyl)propane; 2,2-bis(3,5-disopropyl-4-hydroxyphenyl)propane; 2,2-bis(3,5-di-t-butyl-4-hydroxyphenyl)propane; 2,2-bis(3,5-diphenyl-4-hydroxyphenyl)propane; 2,2-bis(4-hydroxy-2,3,5,6-tetrachlorophenyl)propane; 2,2-bis(4-hydroxy-2,3,5,6-tetrabromophenyl)propane; 2,2-bis(4-hydroxy-2,3,5,6-tetramethylphenyl)propane; 2,2-bis(2,6-dichloro-3,5-dimethyl-4-hydroxyphenyl)propane; 2,2-bis(2,6-dibromo-3,5-dimethyl-4-hydroxyphenyl)propane; 2,2-bis(4-hydroxy-3-ethylphenyl)propane; 2,2-bis(4-hydroxy-3,5-dimethylphenyl)propane; 2,2-bis(3,5,3',5'-tetrachloro-4,4'-dihydroxyphenyl)propane; 1,1-bis(4-hydroxyphenyl) cyclohexylmethane; 2,2-bis(4-hydroxyphenyl)-1-phenylpropane; 1,1-bis(4-hydroxyphenyl)cyclohexane; 1,1-bis(3-chloro-4-hydroxyphenyl)cyclohexane; 1,1-bis(3-bromo-4-hydroxyphenyl)cyclohexane; 1,1-bis(4-hydroxy-3-methylphenyl)cyclohexane; 1,1-bis(4-hydroxy-3-isopropylphenyl)cyclohexane; 1,1-bis(3-t-butyl-4-hydroxyphenyl)cyclohexane; 1,1-bis(3-phenyl-4-hydroxyphenyl)cyclohexane; 1,1-bis(3,5-dichloro-4-hydroxyphenyl)cyclohexane; 1,1-bis(3,5-dibromo-4-hydroxyphenyl)cyclohexane; 1,1-bis(3,5-dimethyl-4-hydroxyphenyl)cyclohexane; 4,4'-[1-methyl-4-(1-methylethyl)-1,3-cyclohexandiyl]bisphenol (1,3 BHPM); 4-[1-[3-(4-hydroxyphenyl)-4-methylcyclohexyl]-1-methyl-ethyl]-phenol (2,8 BHPM); 3,8-dihydroxy-5a,10b-diphenylcoumarano-2',3',2,3-coumarane (DCBP); 2-phenyl-3,3-bis(4-hydroxyphenyl)phthalimidine; 1,1-bis(3-chloro-4-hydroxy-5-methylphenyl)cyclohexane; 1,1-bis(3-bromo-4-hydroxy-5-methylphenyl)cyclohexane; 1,1-bis(3-chloro-4-hydroxy-5-isopropylphenyl)cyclohexane; 1,1-bis(3-bromo-4-hydroxy-5-isopropylphenyl)cyclohexane; 1,1-bis(3-t-butyl-5-chloro-4-hydroxyphenyl)cyclohexane; 1,1-bis(3-bromo-5-t-butyl-4-hydroxyphenyl)cyclohexane; 1,1-bis(3-chloro-5-phenyl-4-hydroxyphenyl)cyclohexane; 1,1-bis(3-bromo-5-phenyl-4-hydroxyphenyl)cyclohexane; 1,1-bis(3,5-disopropyl-4-hydroxyphenyl)cyclohexane; 1,1-bis(3,5-di-t-butyl-4-hydroxyphenyl)cyclohexane; 1,1-bis(3,5-diphenyl-4-hydroxyphenyl)cyclohexane; 1,1-bis(4-hydroxy-2,3,5,6-tetrachlorophenyl)cyclohexane; 1,1-bis(4-hydroxy-2,3,5,6-tetrabromophenyl)cyclohexane; 1,1-bis(4-hydroxy-2,3,5,6-tetramethylphenyl)cyclohexane; 1,1-bis(2,6-dichloro-3,5-dimethyl-4-hydroxyphenyl)cyclohexane; 1,1-bis(2,6-dibromo-3,5-dimethyl-4-hydroxyphenyl)cyclohexane; 1,1-bis(4-hydroxyphenyl)-3,3,5-trimethylcyclohexane; 1,1-bis(3-chloro-4-hydroxyphenyl)-3,3,5-trimethylcyclohexane; 1,1-bis(3-bromo-4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis(3-phenyl-4-hydroxyphenyl)-3,3,5-trimethylcyclohexane; 1,1-bis(3,5-dichloro-4-hydroxyphenyl)-3,3,5-trimethylcyclohexane; 1,1-bis(3,5-dibromo-4-hydroxyphenyl)-3,3,5-trimethylcyclohexane; 1,1-bis(3,5-dimethyl-4-hydroxyphenyl)-3,3,5-trimethylcyclohexane; 1,1-bis(3-chloro-4-hydroxy-5-methylphenyl)-3,3,5-trimethylcyclohexane; 1,1-bis(3-bromo-4-hydroxy-5-methylphenyl)-3,3,5-trimethylcyclohexane; 1,1-bis(3-chloro-4-hydroxy-5-isopropylphenyl)-3,3,5-trimethylcyclohexane; 1,1-bis(3-bromo-4-hydroxy-5-isopropylphenyl)-3,3,5-trimethylcyclohexane; 1,1-bis(3-t-butyl-5-chloro-4-hydroxyphenyl)-3,3,5-trimethylcyclohexane; 1,1-bis(3-bromo-5-t-butyl-4-hydroxyphenyl)-3,3,5-trimethylcyclohexane; bis(3-chloro-5-phenyl-4-hydroxyphenyl)-3,3,5-trimethylcyclohexane; 1,1-bis(3-bromo-5-phenyl-4-hydroxyphenyl)-3,3,5-trimethylcyclohexane; 1,1-bis(3,5-disopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetrachlorophenyl)-3,3,5-trimethylcyclohexane; 1,1-bis(4-hydroxy-2,3,5,6-tetrabromophenyl)-3,3,5-trimethylcyclohexane; 1,1-bis(4-hydroxy-2,3,5,6-tetramethylphenyl)-3,3,5-trimethylcyclohexane; 1,1-bis(2,6-dichloro-3,5-dimethyl-4-hydroxyphenyl)-3,3,5-trimethylcyclohexane; 1,1-bis(2,6-dibromo-3,5-dimethyl-4-hydroxyphenyl)-3,3,5-trimethylcyclohexane; 4,4-bis(4-hydroxyphenyl)heptane; 1,1-bis(4-hydroxyphenyl)decane; 1,1-bis(4-hydroxyphenyl) cyclododecane; 1,1-bis(3,5-dimethyl-4-hydroxyphenyl)cyclododecane; 4,4'dihydroxy-1,1-biphenyl; 4,4'-dihydroxy-3,3'-dimethyl-1,1-biphenyl; 4,4'-dihydroxy-3,3'-dioctyl-1,1-biphenyl; 4,4'-(3,3,5-trimethylcyclohexylidene)diphenol; 4,4'-bis(3,5-dimethyl)diphenol; 4,4'-dihydroxydiphenylether; 4,4'-dihydroxydiphenylthioether; 1,3-bis(2-(4-hydroxyphenyl)-2-propyl)benzene; 1,3-bis(2-(4-hydroxy-3-methylphenyl)-2-propyl)benzene; 1,4-bis(2-(4-hydroxyphenyl)-2-propyl)benzene; 1,4-bis(2-(4-hydroxy-3-methylphenyl)-2-propyl)benzene; 2,4'-dihydroxyphenyl sulfone; 4,4'-dihydroxydiphenylsulfone (BPS); bis(4-hydroxyphenyl)methane; 2,6-dihydroxy naphthalene; hydroquinone; resorcinol; $C_{1-3}$ alkyl-substituted resorcinols; 3-(4-hydroxyphenyl)-1,1,3-trimethylindan-5-ol; 1-(4-hydroxyphenyl)-1,3,3-trimethylindan-5-ol; 4,4-dihydroxydiphenyl ether; 4,4-dihydroxy-3,3-dichlorodiphenylether; 4,4-dihydroxy-2,5-dihydroxydiphenyl ether; 4,4-thiodiphenol; 2,2,2',2'-tetrahydro-3,3,3',3'-tetramethyl-1,1'-spirobi[1H-indene]-6,6'-diol; and mixtures thereof.

In one embodiment of the present invention, the polycarbonates prepared using the aromatic chloroformates of the present invention may be further employed to prepare polymer compositions. In one embodiment, the polymer compositions provided by the present invention comprise one or more additional resins selected from the group consisting of polyamides, polyesters, polycarbonates; olefin polymers such as ABS, polystyrene, polyethylene; polysiloxanes, polysilanes and polysulfones. In certain embodiments the one or more additional resins may be present preferably in an amount less than or equal to 40 weight percent, more preferably less than or equal to 35 weight percent and most preferably less than or equal to about 30 weight percent based on the total weight of the polymer composition.

The polymer compositions may contain various additives, which may be used alone or in combination. These additives include such materials as thermal stabilizers, antioxidants, UV stabilizers, plasticizers, visual effect enhancers, extenders, antistatic agents, catalyst quenchers, mold releasing agents, fire retardants, blowing agents, impact modifiers and processing aids. The different additives that can be incorporated in the polymer compositions of the present invention are typically commonly used and known to those skilled in the art.

Visual effect enhancers, sometimes known as visual effects additives or pigments may be present in an encapsulated form, a non-encapsulated form, or laminated to a particle comprising polymeric resin. Some non-limiting examples of visual effects additives are aluminum, gold, silver, copper, nickel, titanium, stainless steel, nickel sulfide, cobalt sulfide, manganese sulfide, metal oxides, white mica, black mica, pearl mica, synthetic mica, mica coated with titanium dioxide, metal-coated glass flakes, and colorants, including but not limited, to Perylene Red. The visual effect additive may have a high or low aspect ratio and may comprise greater than 1 facet. Dyes may be employed such as Solvent Blue 35, Solvent Blue 36, Disperse Violet 26, Solvent Green 3, Anaplast Orange LFP, Perylene Red, and Morplas Red 36. Fluorescent dyes may also be employed including, but not limited to, Permanent Pink R (Color Index Pigment Red 181, from Clariant Corporation), Hostasol Red 5B (Color Index #73300, CAS # 522-75-8, from Clariant Corporation) and Macrolex Fluorescent Yellow 10GN (Color Index Solvent Yellow 160:1, from Bayer Corporation). Pigments such as titanium dioxide, zinc sulfide, carbon black, cobalt chromate, cobalt titanate, cadmium sulfides, iron oxide, sodium aluminum sulfosilicate, sodium sulfosilicate, chrome antimony titanium rutile, nickel antimony titanium rutile, and zinc oxide may be employed. Visual effect additives in encapsulated form usually comprise a visual effect material such as a high aspect ratio material like aluminum flakes encapsulated by a polymer. The encapsulated visual effect additive has the shape of a bead.

Non-limiting examples of antioxidants that can be used in the polymer compositions of the present invention include tris(2,4-di-tert-butylphenyl)phosphite; 3,9-di(2,4-di-tert-butylphenoxy)-2,4,8,10-tetraoxa-3,9-diphosphaspiro[5.5]undecane; 3,9-di(2,4-dicumylphenoxy)-2,4,8,10-tetraoxa-3,9-diphosphaspiro[5.5]undecane; tris(p-nonylphenyl) phosphite; 2,2',2"-nitrilo[triethyl-tris[3,3',5,5'-tetra-tertbutyl-1,1'-biphenyl-2'-diyl]phosphite]; 3,9-distearyloxy-2,4,8,10-tetraoxa-3,9-diphosphaspiro[5.5]undecane; dilauryl phosphite; 3,9-di[2,6-di-tert-butyl-4-methylphenoxy]-2,4,8,10-tetraoxa-3,9-diphosphaspiro[5.5]undecane; tetrakis(2,4-di-tert-butylphenyl)-4,4'-bis(diphenylene)phosphonite; distearyl pentaerythritol diphosphite; diisodecyl pentaerythritol diphosphite; 2,4,6-tri-tert-butylphenyl-2-butyl-2-ethyl-1,3-propanediol phosphite; tristearyl sorbitol triphosphite; tetrakis(2,4-di-tert-butylphenyl)-4,4'-biphenylene diphosphonite; (2,4,6-tri-tert-butylphenyl)-2-butyl-2-ethyl-1,3-propanediolphosphite; triisodecylphosphite; and mixtures of phosphites containing at least one of the foregoing.

The thermoplastic composition may optionally comprise an impact modifier. The impact modifier resin added to the thermoplastic composition in an amount corresponding to about 1% to about 30% by weight, based on the total weight of the composition. Suitable impact modifiers include those comprising one of several different rubbery modifiers such as graft or core shell rubbers or combinations of two or more of these modifiers. Impact modifiers are illustrated by acrylic rubber, ASA rubber, diene rubber, organosiloxane rubber, ethylene propylene diene monomer (EPDM) rubber, styrene-butadiene-styrene (SBS) rubber, styrene-ethylene-butadiene-styrene (SEBS) rubber, acrylonitrile-butadiene-styrene (ABS) rubber, methacrylate-butadiene-styrene (MBS) rubber, styrene acrylonitrile copolymer and glycidyl ester impact modifier.

The term "acrylic rubber modifier" may refer to multi-stage, core-shell, interpolymer modifiers having a cross-linked or partially crosslinked (meth)acrylate rubbery core phase, preferably butyl acrylate. Associated with this cross-linked acrylic ester core is an outer shell of an acrylic or styrenic resin, preferably methyl methacrylate or styrene, which interpenetrates the rubbery core phase. Incorporation of small amounts of other monomers such as acrylonitrile or (meth)acrylonitrile within the resin shell also provides suitable impact modifiers. The interpenetrating network is provided when the monomers forming the resin phase are polymerized and cross-linked in the presence of the previously polymerized and cross-linked (meth)acrylate rubbery phase.

Suitable impact modifiers are graft or core shell structures with a rubbery component with a Tg below 0° C., preferably between about −40° to −80° C., composed of poly alkylacrylates or polyolefins grafted with polymethylmethacrylate (PMMA) or styrene acrylonitrile (SAN). Preferably the rubber content is at least 10 wt %, more preferably greater than 40 wt %, and most preferably between about 40 and 75 wt %.

Other suitable impact modifiers are the butadiene core-shell polymers of the type available from Rohm & Haas, for example Paraloid® EXL2600. Most suitable impact modifier will comprise a two stage polymer having a butadiene based rubbery core and a second stage polymerized from methylmethacrylate alone or in combination with styrene. Other suitable rubbers are the ABS types Blendex® 336 and 415, available from GE Specialty Chemicals. Both rubbers are based on impact modifier resin of SBR rubber. Although several rubbers have been described, many more are commercially available. Any rubber may be used as an impact modifier as long as the impact modifier does not negatively impact the physical or aesthetic properties of the thermoplastic composition.

Non-limiting examples of processing aids that can be used include Doverlube® FL-599 (available from Dover Chemical Corporation), Polyoxyter® (available from Polychem Alloy Inc.), Glycolube P (available from Lonza Chemical Company), pentaerythritol tetrastearate, Metablen A-3000 (available from Mitsubishi Rayon), neopentyl glycol dibenzoate, and the like.

Non-limiting examples of UV stabilizers that can be used include 2-(2'-Hydroxyphenyl)-benzotriazoles, e.g., the 5'-methyl-; 3',5'-di tert.-butyl-; 5'-tert.-butyl-; 5'-(1,1,3,3-tetramethylbutyl)-; 5-chloro-3',5'-di-tert.-butyl-; 5-chloro-3'-tert.-butyl-5'-methyl-; 3'-sec.-butyl-5'-tert.-butyl-; 3'-alpha-methylbenzyl-5'-methyl; 3'-alpha-methylbenzyl-5'-methyl-5-chloro-; 4'-hydroxy-; 4'-methoxy-; 4'-octoxy-; 3',5'-di-tert.-amyl-; 3'-methyl-5'-carbomethoxyethyl-; 5-chloro-3',5'-di-tert.-amyl-derivatives; and Tinuvin® 234 (available from Ciba Specialty Chemicals). Also suitable are the 2,4-bis-(2'-hydroxyphenyl)-6-alkyl-s-triazines, e.g., the 6-ethyl-; 6heptadecyl- or 6-undecyl-derivatives. 2-Hydroxy-benzophenones e.g., the 4-hydroxy-; 4-methoxy-; 4-octoxy-; 4decyloxy-; 4-dodecyloxy-; 4-benzyloxy-; 4,2',4'-trihydroxy-; 2,2',4,4'-tetrahydroxy- or 2'-hydroxy-4,4'-dimethoxy-derivative. 1,3-bis-(2'-Hydroxybenzoyl)-benzenes, e.g., 1,3-bis-(2'-hydroxy-4'-hexyloxy-benzoyl)-benzene; 1,3-bis-(2'-hydroxy-4'-octyloxy-benzoyl)-benzene or 1,3-bis-(2'-hydroxy-4'-dodecyloxybenzoyl)-benzene may also be employed. Esters of optionally substituted benzoic acids, e.g., phenylsalicylate; octylphenylsalicylate; dibenzoylresorcin; bis-(4-tert.-butylbenzoyl)-resorcin; benzoylresorcin; 3,5-di-tert.-butyl-4-hydroxybenzoic acid-2,4di-tert.-butylphenyl ester or -octadecyl ester or -2-methyl-4,6-di-tert. butyl ester may likewise be employed. Acrylates, e.g., alpha-cyano beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or -butyl ester or N(beta-carbomethoxyvinyl)-2-methyl-indoline may likewise be employed. Oxalic acid diamides, e.g., 4,4'-di-octyloxy-oxanilide; 2,2'-di octyloxy-5,5'-di-tert.-butyl-oxanilide; 2,2'-di-dodecyloxy-5,5-di-tert. butyl-oxanilide; 2-ethoxy-2'-ethyl-oxanilide; N,N'-bis-(3-dimethyl aminopropyl)-oxalamide; 2-ethoxy-5-tert.-butyl-2'-ethyloxanilide and the mixture thereof with 2-ethoxy-2'-ethyl-5,4'-di-tert.-butyl-oxanilide; or mixtures of ortho- and para-methoxy- as well as of o- and p-ethoxy-disubstituted oxanilides are also suitable as UV stabilizers. Preferably the ultraviolet light absorber used in the instant compositions is 2-(2-hydroxy-5-methylphenyl)-2H-benzotriazole; 2-(2-hydroxy-3,5-di-tert-amylphenyl)-2H-benzotriazole; 2-[2-hydroxy-3,5-di-(alpha,alpha-dimethylbenzyl)phenyl]-2H-benzotriazole; 2-(2-hydroxy-5-tert-octylphenyl)-2H-benzotriazole; 2-hydroxy-4-octyloxybenzophenone; nickel bis(O-ethyl 3,5-di-tert-butyl-4-hydroxybenzylphosphonate); 2,4-dihydroxybenzophenone; 2-(2-hydroxy-3-tert-butyl-5-methylphenyl)-2H-benzotriazole; nickel butylamine complex with 2,2'-thiobis(4-tert-butylphenol); 2-ethoxy-2'-ethyloxanilide; 2-ethoxy-2'-ethyl-5,5'-ditert-butyloxanilide or a mixture thereof.

Non-limiting examples of fire retardants that can be used include potassium diphenylsulfone sulfonate, and phosphite esters of polyhydric phenols, such as resorcinol and bisphenol A.

Non-limiting examples of mold release compositions include esters of long-chain aliphatic acids and alcohols such as pentaerythritol, guerbet alcohols, long-chain ketones, siloxanes, alpha.-olefin polymers, long-chain alkanes and hydrocarbons having 15 to 600 carbon atoms.

It should be noted that in certain embodiments of the present invention, the degree to which the aromatic hydroxyl group undergoing chloroformylation is sterically hindered may act to greatly reduce the rate of chloroformylation. In certain instances, for example, the rate of choroformylation may be such that no reaction product is observed under reaction conditions which typically provide excellent yields of representative hindered phenols such as 2,6-dimethylphenol and 2,6-diphenylphenol. Thus, in one embodiment, the present invention provides a method for preparing an aromatic chloroformate from an aromatic hydroxyl compound that is not a aromatic hydroxyl compound comprising only hydroxyl groups flanked on each side by tertiary aliphatic and/or tertiary cycloaliphatic radicals. In yet another embodiment the present invention provides a method for preparing an aromatic chloroformate from an aromatic hydroxyl compound having formula III

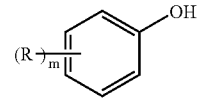

Formula III wherein R is independently at each occurrence a hydrogen atom, a $C_1$-$C_{25}$ aliphatic radical, a $C_3$-$C_{20}$ cycloaliphatic radical or a $C_3$-$C_{20}$ aromatic radical, and "m" is an integer having value 0 to 5, and wherein said aromatic hydroxyl compound is not a mono-hydroxy aromatic compound in which the hydroxyl group of formula III is flanked on each side by tertiary aliphatic and/or tertiary cycloaliphatic radicals. Aromatic hydroxyl compounds having formula III that are flanked on each side by tertiary aliphatic and/or tertiary cycloaliphatic radicals are illustrated by 2-(adamant-1'-yl)-6-t-butyl phenol; 2,6-di-t-butylphenol, and the like.

EXAMPLES

The following examples are set forth to provide those of ordinary skill in the art with a detailed description of how the methods claimed herein are evaluated, and are not intended to limit the scope of what the inventors regard as their invention. Unless indicated otherwise, parts are by weight, temperature is in ° C.

Molecular weights are reported as number average ($M_n$) or weight average ($M_w$) molecular weight and were determined by gel permeation chromatography (GPC) analysis, using polystyrene molecular weight standards to construct a standard calibration curve against which polymer molecular weights were determined. The temperature of the gel permeation columns was about 25° C. and the mobile phase was chloroform.

In interfacial polymerization reactions a Mettler glass electrode was used to maintain the pH at the appropriate value. The electrode was calibrated at pH 7 and pH 10 using standard pH buffer solutions.

Examples 1-3

The following general procedure was used for the preparation of aromatic chloroformates in Examples 1-3. A feed solution of the aromatic hydroxyl compound (2,6-dimethylphenol, 2,6-diphenylphenol or 2,6-ditert-butylphenol) in methylene chloride was prepared. An appropriate level of triethylamine organic base was added to this solution. The feed solution was fed into the reactor at the rate of 30 gm/min. Phosgene was introduced into the reactor at the rate of 2.91 gm/min, independent of other reactants. All feeds were at room temperature (25° C.) and the reactor was not insulated. The flow reactor employed typically comprised a series of five Ko-Flo® static mixers (7 inches by ¼ inches each). The total reactor volume was about 15 milliliters. Residence time in the flow reactor varied depending on the flow rates of the components being fed and number of mixing sections used. The reaction product was collected in a 100 milliliter 3-neck round bottom flask that initially contained 50 milliliters of 1N HCl. Approximately 30 milliliters of product solution was collected and analyzed by $^1$H-NMR. Data showing the amounts of reactants used and the yields of aromatic chloroformates obtained are given in Table 1 below.

TABLE 1

PREPARATION OF AROMATIC CHLOROFORMATES

| Example | Aromatic Hydroxyl Compound | Amount of Aromatic Hydroxyl Compound in grams | Amount of TEA in grams | Amount of Methylene Chloride in grams | Percent Conversion to chloroformate |
|---|---|---|---|---|---|
| 1 | 2,6 dimethylphenol | 9.278 | 10.62 | 300 | 85 |
| 2 | 2,6 diphenylphenol | 9.278 | 5.27 | 300 | 100 |
| 3 | 2,6 di-t-butylphenol | 9.278 | 6.29 | 300 | 0 |

Examples 1-2 demonstrate that the process of the present invention, generally affords high conversion of phenols to the corresponding chloroformates with essentially no byproduct carbonate formation. It should be noted that the experiments conducted as part of this study were not optimized in all cases. Example 3 suggests that for aromatic hydroxyl compounds in which the aromatic hydroxyl group is flanked by 2 tertiary aliphatic groups, chloroformate formation is slow. This observation suggests that it is possible to effect selective chloroformylation of relatively less hindered phenols (2,6-dimethylphenol) and/or relatively more acidic phenols (2,6-diphenylphenol) in mixed systems comprising multiple aromatic hydroxyl compounds. Moreover, this observation suggests that selective chloroformylation of relatively less hindered hydroxyl groups and/or relatively more acidic hydroxyl groups occurs in instances in which the aromatic hydroxyl compound comprises multiple hydroxyl groups having different steric environments and/or acidities.

Example 4

The experimental set up used in this example consisted of a batch reactor for preparing a polycarbonate and flow reactor for preparing the chloroformate of a phenol. The batch reactor used was a 2-liter agitated batch reaction vessel equipped with a pH electrode, a dip tube, a tube for addition of 50 wt percent sodium hydroxide solution and a reflux condenser. The batch reactor was initially maintained at room temperature. A dual 6-blade turbine impeller operated at 450 revolutions per minute was used as the agitator. The flow reactor employed typically comprised a series of two 316SS Ko-Flo® static mixers (⅜" o.d.×11" long) which were insulated. The output of the flow reactor was connected to the diptube of the batch reactor. The 2-liter batch reactor was charged with 140 grams bisphenol A, 650 milliliters methylene chloride, and 425 milliliters H₂O. Phosgene (12.1 grams) was introduced at the rate of 3.0 grams/minute through the flow reactor connected to the dip tube of the batch reactor. After the addition of phosgene (12.1 g), a feed solution (112.3 g) comprising 3.0 wt percent 2,6-dimethyl phenol and 2.48 wt percent triethylamine in methylene chloride was introduced into the flow reactor at a rate of 30.8 g/min, while continuing the addition of phosgene into the flow reactor. The product stream emerging from the flow reactor was introduced into the batch reactor via the dip tube. The pH in the batch reactor was maintained at about 10.5 by addition of 50 wt. percent sodium hydroxide. After the addition of the feed solution, a methylene chloride flush stream was introduced into the flow reactor at about 30 g/min for 2 minutes while continuing the flow of phosgene through the flow reactor and into the batch reactor. The addition of the phosgene stream continued uninterrupted through the flow reactor until 74.4 gm phosgene was added to the batch reactor. After the addition of phosgene was completed, 0.25 gm/min nitrogen was purged through the phosgene feed line and tube reactor and into the batch reactor, and the reaction was agitated for 15 minutes. The reaction product was then quenched with 1N HCl, washed three times with deionized water, and then analyzed by proton nuclear magnetic resonance ($^1$H-NMR) and gel permeation chromatography (GPC). $^1$H-NMR showed excellent incorporation of the 2,6-dimethylphenol as endgroups of the product polycarbonate. The polycarbonate product molecular weight based on polystyrene standards was 24,500 ($M_n$) and 79,800 ($M_w$).

Example 4 demonstrates that the hindered phenol (2,6-dimethylphenol) was efficiently incorporated into the polycarbonate.

Comparative Example 1

This experiment employed a batch reactor apparatus similar to that used in Example 4 except that there was no flow reactor connected to the dip tube. The batch reactor was charged with charged with 140 grams bisphenol A, 650 milliliters methylene chloride, and 425 milliliters H₂O. Phosgene (74.5 g) was added directly to the batch reactor at the rate of 3 g/min via the dip tube. After 12.1 gm phosgene was added, a feed solution (112.3 g) consisting of 3 wt. percent 2,6-dimethylphenol and 2.48 weight percent triethylamine in methylene chloride was added to the batch reactor at the rate of 30.8 grams per minute. Addition of phosgene was continued during the addition of the feed solution. The pH of the reactor was maintained at about 10.5 by the addition of 50 wt. percent aqueous sodium hydroxide. After the addition of phosgene was completed, 0.25 gm/min nitrogen was purged through the phosgene feed line and the batch reactor, and the reaction was agitated for 15 minutes. The reaction product was then quenched with 1N HCl, washed three times with deionized water, and then analyzed by proton NMR and gel permeation chromatography (GPC). Proton NMR showed poor incorporation of the 2,6-dimethyl phenol into the polycarbonate. The product molecular weight based on polystyrene standards was 42,100 ($M_n$) and 237,200 ($M_w$).

The higher molecular weight obtained in Comparative Example 1 demonstrates that the 2,6-dimethyl phenol end cap was poorly incorporated into the polycarbonate.

The invention has been described in detail with particular reference to preferred embodiments thereof, but it will be understood by those skilled in the art that variations and modifications can be effected within the spirit and scope of the invention.

What is claimed is:

1. A method of preparing an aromatic chloroformate, said method comprising:
   (a) introducing into a flow reactor at least one aromatic hydroxyl compound, phosgene, at least one solvent, and at least one organic base to form a unidirectionally flowing reaction mixture, said unidirectionally flowing reaction mixture being substantially free of water; and (b) maintaining said unidirectionally flowing reaction mixture at a temperature in a range between about 0° C. and about 60° C. to produce a product stream comprising an aromatic chloroformate.

2. The method according to claim 1 wherein said aromatic hydroxyl compound comprises structural units having formula I $$(R)_m\text{-}Q\text{-}(OH)_n \qquad \text{Formula I}$$

wherein Q is a $C_3$-$C_{20}$ aromatic radical, R is independently at each occurrence a hydrogen atom, a $C_1$-$C_5$ aliphatic radical, a $C_3$-$C_7$ cycloaliphatic radical or a $C_3$-$C_6$ aromatic radical, "n" is a number equal to the total number of aromatic positions on Q available for substitution and "m" is an integer having value 0 to {(the total number of positions on Q available for substitution)-n }.

3. The method according to claim 1 wherein said aromatic chloroformate comprises at least one chloroformate selected from the group consisting of monochloroformates, bischloroformates, trischloroformates, and polychlororformates.

4. The method according to claim 3 wherein said aromatic chloroformate is a monochloroformate.

5. The method according to claim 1 wherein said unidirectionally flowing reaction mixture comprises less than 1% by weight water.

6. The method according to claim 1 wherein said solvent is selected from the group consisting of aliphatic solvents and aromatic solvents.

7. The method according to claim 6 wherein said solvent is selected from the group consisting of chlorinated aliphatic solvents.

8. The method according to claim 7 wherein said solvent is methylene chloride.

9. The method according to claim 1 wherein said organic base is selected from the group consisting of amine bases and polyamine bases.

10. The method according to claim 1 wherein said unidirectionally flowing reaction mixture is characterized by a molar ratio of phosgene to the aromatic hydroxyl groups, said ratio being in a range of from about 1.1 to about 100 to 1.

11. The method according to claim 10 wherein said unidirectionally flowing reaction mixture is characterized by a molar ratio of phosgene to the aromatic hydroxyl groups, said ratio being in a range of from about 1.1 to about 5 to 1.

12. The method according to claim 1 wherein said unidirectionally flowing reaction mixture is characterized by a molar ratio of the organic base to the aromatic hydroxyl groups, said ratio being in a range of from about 0.01 to about 100 to 1.

13. The method according to claim 12 wherein said unidirectionally flowing reaction mixture is characterized by a molar ratio of the organic base to the aromatic hydroxyl groups, said ratio being in a range of from about 0.01 to 1 to about 5 to 1.

14. The method according to claim 13 wherein said unidirectionally flowing reaction mixture is characterized by a molar ratio of the organic base to the aromatic hydroxyl groups, said ratio being in a range of from about 0.01 to about 1.1 to 1.

15. The method according to claim 1 wherein said product stream is a single product stream.

16. The method according to claim 1 wherein said temperature is in a range between about 10° C. and about 50° C.

17. The method according to claim 1 wherein said flow reactor is a tubular reactor.

18. A method for preparing a co-polycarbonate said method comprising reacting at least one dihydroxy aromatic compound under interfacial conditions with phosgene and an aromatic chloroformate, said aromatic chloroformate being prepared by a method comprising;

(a) introducing into a flow reactor at least one aromatic hydroxyl compound, phosgene, at least one solvent, and an organic base to form a unidirectionally flowing reaction mixture, said unidirectionally flowing reaction mixture being substantially free of water; and (b) maintaining said unidirectionally flowing reaction mixture at a temperature in a range between about 0° C. and about 60° C. to produce a product stream comprising an aromatic chloroformate.

19. The method according to claim 18 wherein the aromatic chloroformate product from the flow reactor is used in its entirety and without purification.

20. The method according to claim 18 wherein said dihydroxy aromatic compound is a bisphenol having formula II;

$$HO\text{-}\!\!\left[G^1\right]_t\!\!\left[E\right]_s\!\!\left[G^1\right]_u\!\!\text{-}OH; \qquad \text{Formula II}$$

wherein each $G^1$ is independently at each occurrence a $C_6$-$C_{20}$ aromatic radical; E is independently at each occurrence a bond, a $C_3$-$C_{20}$ cycloaliphatic radical, a $C_6$-$C_{20}$ aromatic radical, a $C_1$-$C_{20}$ aliphatic radical, a sulfur-containing linkage, a selenium-containing linkage, a phosphorus-containing linkage, or an oxygen atom; "t" is a number greater than or equal to one; "s" is either zero or one; and "u" is a whole number including zero.

21. A method of preparing an aromatic chloroformate, said method comprising:

(a) introducing into a flow reactor at least one aromatic hydroxyl compound, phosgene, at least one solvent, and an organic base to form a unidirectionally flowing reaction mixture, said unidirectionally flowing reaction mixture being substantially free of water; and (b) maintaining said unidirectionally flowing reaction mixture at a temperature in a range between about 0° C. and about 60° C. to produce a product stream comprising an aromatic chloroformate;

wherein said aromatic hydroxyl compound is not a aromatic hydroxyl compound comprising only hydroxyl groups flanked on each side by tertiary aliphatic and/or tertiary cycloaliphatic radicals.

22. A method of preparing an aromatic chloroformate, said method comprising:

(a) introducing into a flow reactor at least one aromatic hydroxyl compound, phosgene, at least one solvent, and at least one organic base to form a unidirectionally flowing reaction mixture, said unidirectionally flowing reaction mixture being substantially free of water, wherein said aromatic hydroxyl compound has formula III;

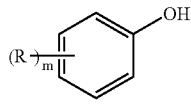

Formula III wherein R is independently at each occurrence a hydrogen atom, a $C_1$-$C_{25}$ aliphatic radical, a $C_3$-$C_{20}$ cycloaliphatic radical or a $C_3$-$C_{20}$ aromatic radical, and "m" is an integer having value 0 to 5, and wherein said aromatic hydroxyl compound is not a mono-hydroxy aromatic compound in which the hydroxyl group of formula III is flanked on each side by tertiary aliphatic and/or tertiary cycloaliphatic radicals; and (b) maintaining said unidirectionally flowing reaction mixture at a temperature in a range between about 0° C. and about 60° C. to produce a product stream comprising an aromatic chloroformate.

* * * * *